United States Patent
Twu et al.

(12) 
(10) Patent No.: US 6,407,302 B1
(45) Date of Patent: Jun. 18, 2002

(54) ISOMERIZATION PROCESS OF A MIXTURE CONTAINING VINYL AND VINYLIDENE OLEFINS

(75) Inventors: Fred Chun-Chien Twu, Naperville, IL (US); William L. Cox, Houston, TX (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/479,175

(22) Filed: Jan. 7, 2000

Related U.S. Application Data

(63) Continuation-in-part of application No. 09/433,662, filed on Nov. 4, 1999, now abandoned.

(51) Int. Cl.$^7$ .............................. C07C 5/23; C07C 5/25
(52) U.S. Cl. ..................... 585/670; 585/664; 585/670
(58) Field of Search ................................. 585/670, 664, 585/16; 502/355

(56) References Cited

U.S. PATENT DOCUMENTS

| | | | | |
|---|---|---|---|---|
| 4,229,610 A | * | 10/1980 | Myers et al. | 585/664 |
| 4,587,374 A | * | 5/1986 | Peters | 585/670 |

FOREIGN PATENT DOCUMENTS

| | | | |
|---|---|---|---|
| GB | 2129701 A | * | 5/1984 |

* cited by examiner

*Primary Examiner*—Thuan D. Dang
(74) *Attorney, Agent, or Firm*—James R. Henes

(57) ABSTRACT

A method for the isomerization of a mixture of vinyl and vinylidene olefins having 10 to 35 carbons atoms to form a mixture comprising both di- and tri-substituted internal olefins including deep internal olefins.

12 Claims, No Drawings

ISOMERIZATION PROCESS OF A MIXTURE CONTAINING VINYL AND VINYLIDENE OLEFINS

RELATED APPLICATION

This application is a continuation-in-part of copending U.S. patent application Ser. No. 09/433,662, filed Nov. 4, 1999 now abandoned.

FIELD OF THE INVENTION

The present invention relates to the isomerization of olefins and more particularly concerns the isomerization of a mixture of vinyl and vinylidene olefins.

BACKGROUND OF THE INVENTION

Mixtures of linear terminal mono-olefins, commonly referred to as linear alpha-olefins, are made commercially by ethylene chain growth of aluminum alkyls followed by displacement. Such products are mainly vinyl-olefins having the structure:

Formula 1 wherein $R^1$ is an aliphatic hydrocarbon group. These olefins are referred to as "vinyl olefins". In addition, a substantial portion of the alpha-olefins can be in the form of "vinylidene olefins" which have the structure:

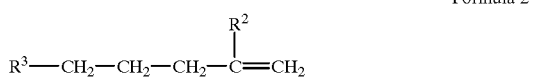

Formula 2 wherein $R^2$ and $R^3$ are aliphatic hydrocarbon groups which may be the same or different.

For many applications, it is highly desirable to use linear internal olefins. Linear internal olefins can be made from alpha-olefins by isomerizing the olefinic double bond from a terminal to an internal position. Such linear internal olefins can be represented by Formulas 3, 4, 5, or 6,

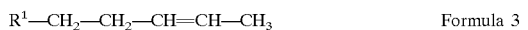 Formula 3

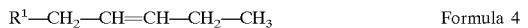 Formula 4

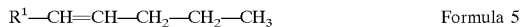 Formula 5

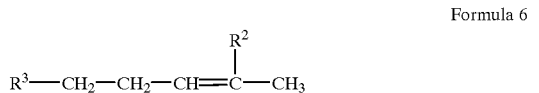 Formula 6

$R^1$ in Formulas 3, 4 and 5 is as defined for Formula 1, and $R_2$ and $R_3$ in Formula 6 are as defined for Formula 2. Olefins having the structures of Formulas-3, 4 and 5 are known as "di-substituted" internal olefins. Olefins having the structure of Formula 6 are known as "tri-substituted" internal olefins. In Formulas 3 and 4, the olefinic double bond is at the second numbered and third numbered carbon atoms, respectively. In Formula 5, the olefinic double bond is at the fourth numbered carbon atom. Internal olefins in which the olefinic double bond is at the fourth or higher (for example, fifth or sixth) numbered carbon atom are called "deep" internal olefins.

Peters, U.S. Pat. No. 4,587,374 discloses that when this is done with the use of alumina or silica/alumina as an isomerization catalyst, a major portion of the olefin groups of the vinylidene olefins are isomerized to the adjacent carbon-carbon bond, thereby forming "tri-substituted" internal olefins. Brennan et. al., U.S. Pat. No. 3,864,424, discloses that, while the use of alumina or a combination of alumina and a strong acid as an isomerization catalyst is capable of isomerizing an olefinic double bond involving a tertiary carbon atom to one involving secondary carbon atoms, the use of a partially dehydrated weakly acidic alumina catalyst effects isomerization of an olefinic double bond involving a tertiary carbon atom to form trisubstituted ethylenes without any appreciable further isomerization to 1,2-disubstituted olefins and without the formation of dimers with other double bonded molecules. In addition, Myers, U.S. Pat. No. 4,225,419, discloses that alumina catalysts are effective in the skeletal isomerization of olefins to more highly branched olefins.

Thus far, there has been no disclosure of a method for the isomerization of alpha olefins to form a product having the desirable features of comprisi di- and tri-substituted internal olefins, and having a greater degree of branching, a kinematic viscosity less than 4 Cst measured at 40° C. and a pour point below –25° C., and comprising at least 20 weight percent of "deep" internal olefins, that is, internal olefins in which the olefinic double bond does not involve a second or third numbered carbon atom.

OBJECTS OF THE INVENTION

It is therefore a general object of the present invention to provide an improved process for the isomerization of a mixture of vinyl and vinylidene olefins that affords a product having the aforesaid desirable features.

More particularly, it is an object of the present invention to provide an aforesaid process in which a mixture of vinyl and vinylidene olefins is isomerized to form a mixture comprising both di- and tri-substituted internal olefins, having a greater degree of branching and at least 20 weight percent of deep internal olefins.

It is another object of the present invention to provide an improved aforesaid isomerization process that produces an isomerization product having a viscosity less than 4 cSt measured at 40° C. and a pour point below –25°.

Other objects and advantages of the present invention will become apparent upon reading the following detailed description and appended claims.

SUMMARY OF THE INVENTION

These objects are achieved by the isomerization method of the present invention, comprising: contacting a linear alpha-olefin mixture comprising vinyl and vinylidene olefins containing from 10 to 35 carbon atoms in the gas or liquid phase with a bed of porous solid acid catalyst particles comprising gamma alumina having a specific surface area of at least 100 square meters per gram, a pore volume of at least 0.4 cubic centimeter per gram, an average pore diameter of at least 30 Angstroms, a sodium content of less than 0.01 weight percent and an ammonia chemisorption of at least 0.1 millimole per gram, at a reaction temperature in the range of from about 200° C. to about 400° C., a reaction pressure in the range of from about 15 to about 500 pounds per square inch absolute and a weight hourly space velocity of from about 0.5 to about 20 pounds of the olefin mixture per pound of catalyst particles per hour, wherein the reaction temperature, pressure and weight hourly space velocity are selected so as to form a product mixture comprising at least 70 weight percent of di- and tri-substituted internal olefins, of which product mixture at least 20 weight percent are tri-substituted internal olefins, at least 20 weight percent are di-substituted internal olefins having a double bond at the fourth or higher numbered carbon atom position and less than 50 weight percent are di-substituted internal olefins having a double bond at the second or third numbered carbon atom position, and which has a kinematic viscosity less than 4 cSt measured at 40° C. and a pour point below −25° C.

The present invention is also the product of the aforesaid process, a mixture having the composition of the aforesaid product and a drilling fluid at least a portion of whose base oil comprises at least a portion of such product or mixture.

DESCRIPTION OF THE PREFERRED EMBODIMENTS

The feedstock employed in the method of the present invention comprises a mixture-of alpha olefins comprising vinyl and vinylidene olefins of Formulas 1 and 2 and having from 10 to 35 carbon atoms. The alpha olefin mixture preferably comprises, and more preferably consists essentially of, olefins containing from 16 to 18 carbon atoms. Although such a mixture is obtainable from a variety of sources, one suitable commercial source is the Ziegler process of triethyl aluminum-ethylene chain growth followed by displacement. Typically, the resultant olefin mixture contains from about 50 to about 95 weight percent of vinyl olefins of Formula 1 and from about 5 to about 50 weight percent of vinylidene olefins of Formula 2. Preferably, olefin mixtures for use as feedstocks for the method of the present invention contain from about 60 to about 90 weight percent of vinyl olefins of Formula 1 and from about 10 to about 40 weight percent of vinylidene olefins of Formula 2.

In Formulas 1, 3, 4 and 5 hereinabove, $R^1$ can contain from 5 to 30 carbon atoms, preferably from 11 to 13 carbon atoms. Examples of these vinyl olefins are 1-decene, 1-dodecene, 1-tetradecene, 1-hexadecene, 1-octadecene, 1-eicosene and the like. In a highly preferred embodiment, the vinyl olefins in the mixtures consist essentially of 1-hexadecene and 1-octadecene. In Formulas 2 and 6, $R^2$ and $R^3$ each contain from 1 to 29 carbon atoms and their sum is in the range of from 5 to 30, preferably from 11 to 13, carbon atoms.

In addition, the initial olefin mixture prior to isomerization in the method of this invention may contain internal olefins. Generally, the amount of internal olefin in the initial mixture is quite low. Typically, amounts of 0 up to about 15 weight percent can be encountered. Generally, the amount of initial internal olefin is about 3-10 weight percent of the olefin mixture, of which very little or none is tri-substituted olefins. Of course, this is exclusive of any internal olefin which might be added to the initial olefin mixture and hence the amount of internal olefins in the isomerization feed is not a critical limitation.

Typical olefin mixtures for use as feedstocks for the method of the present invention are shown in Table I.

TABLE I

| Olefin Mixture | Vinyl Olefin | Vinylidene Olefin | Di-Substituted Internal Olefin |
| --- | --- | --- | --- |
| Dodecenes | 89.1% | 7.5% | 3.4% |
| Hexadecenes | 68.4% | 24.0% | 7.6% |
| Octadecenes | 55.8% | 38.3% | 5.9% |

In the method of the present invention, the feedstock either in the gas or liquid phase is contacted with a bed of solid porous acid catalyst particles comprising gamma alumina. Preferably the catalyst particles contain at least 95 weight percent, more preferably at least 99.5 weight percent, of gamma alumina. Most preferably the catalyst particles consist essentially of gamma alumina. The gamma alumina has a specific surface area of at least 100 square meters per gram, preferably at least 150 square meters per gram, a pore volume of at least 0.4 cubic centimeters per gram, preferably at least 0.5 cubic centimeters per gram, and an average pore diameter of at least 30 Angstroms, preferably at least 40 Angstroms. In addition, the gamma alumina has a sodium content less than 0.01 weight percent and an ammonia chemisorption of at least 0.1 millimole per gram.

The method of the present invention is performed at a temperature in the range of from about 200° C, preferably from about 250° C., more preferably from about 270° C., to about 400° C., preferably to about 350° C, more preferably to about 340° C., at a reaction pressure in the range of from about 15 pounds per square inch absolute to about 500, preferably to about 100, more preferably to about 50, hounds per square inch absolute, and at a weight hourly space velocity of from about 0.5, preferably from about 1, to about 20, preferably to about 15 kilograms of the feed per kilogram of the catalyst particles per hour.

Selection of the reaction temperature and pressure and the weight hourly space velocity from within the aforesaid ranges therefor are made such that a product mixture having the composition set forth hereinbelow of the product of the isomerization method of the present invention and having the pour point and kinematic viscosity set forth hereinbelow is obtained. More particularly, the product of the isomerization method of the present invention is a product mixture comprising di- and tri-substituted internal olefins. Less than 50 weight percent, preferably less than 40 weight percent, of the internal olefins in the aforesaid product mixture have a double bond at the second or third numbered carbon atom position of Formula 3 or 4. At least 20 weight percent, more preferably at least 25 weight percent, of the internal olefins in the aforesaid product mixture involve a double bond at the fourth (of Formula 5) or higher numbered carbon atom position and thus are so-called "deep" olefins. At least 20 weight percent, preferably at least 25 weight percent, of the internal olefins in the aforesaid product mixture are tri-substituted internal olefins of Formula 6. The sum of the concentration of the internal olefins having a double bond at the third numbered carbon atom position (as in Formula 4) plus the concentration of "deep" olefins is preferably at least 45 weight percent, more preferably at least 50 weight percent. The product of the method of the present invention has a kinematic viscosity less than 4 cSt, preferably less than 3.5 cSt, measured at 40° C. and a pour point below −25° C., preferably less than −27° C., preferably less than -30° C.

In addition, in order to obtain the aforesaid product having the aforesaid desirable chemical composition and properties of the product mixture of the method of the present invention, it is highly desirable to limit the extent to which the side reactions of dimerization and cracking occur. A cracked product is one that contains 14 or fewer carbon atoms and is formed during the isomerization process. Thus, the product mixture of the method of this invention preferably contains less than 10 weight percent, more preferably less than 5 weight percent of a dimerization product of an olefin in the feed and less than 10 weight percent, preferably less than 5 weight percent, of a cracked product of an olefin in the feed.

In another respect, the present invention is an olefinic composition formed by any method comprising at least 70 weight percent, of di- and tri-substituted internal olefins having from 10, preferably 16, to 35, preferably to 18, carbon atoms. At least 20 weight percent, preferably at least 25 weight percent, of such composition of the present invention are tri-substituted internal olefins: of Formula 6. Less than 50 weight percent, preferably less than 40 weight percent, of the internal olefins in the composition of the present invention have a double bond involving a number 2 (Formula 3) or number 3 (Formula 4) carbon atom position. At least 20 weight percent, preferably at least 25 weight percent, of the internal olefins have a double bond that involves fourth (Formula 5) or higher numbered atom position. The sum of the concentration of internal olefins having a double bond at the third numbered carbon atom position (as in Formula 4) plus the concentration of "deep" olefins is preferably at least 45 weight percent, more preferably at least 50 weight percent. Such composition of the present invention is further characterized in having a pour point less than −25° C., preferably less than −30° C., and a viscosity measured at 40° C. less than 4 centistokes, preferably less than 3.5 centistokes.

Parameters that are important in selecting base oils that are useful for formulating an invert drilling mud are kinematic viscosity, for example, at 40° C., and pour point. The product of the method of the present invention has a kinematic viscosity and pour point which are such that the product of the method of the present invention is suitable for use as all or a substantial portion of the base oil of an invert drilling mud. Generally invert drilling fluids contain at least 50 volume percent, and typically about 65 to 95 volume percent of a base oil as the continuous phase, up to about 50 volume percent, preferably about 5 to 35 volume percent, of water (which contains up to about 38 weight percent, preferably about 20 to 35 weight percent, of sodium or calcium chloride) and various conventional drilling fluid additives such as emulsifiers, viscosifiers, alkalinity control agents, filtration control agents, oil wetting agents, filtration control agents, oil wetting agents and fluid loss preventing agents. According to this invention, at least about 25 volume percent, preferably at least about 75 volume percent, of the base oil of the drilling fluid comprises the product of the method of this invention (or of the composition of this invention).

The water in oil emulsion is formed by vigorously mixing the base oil together with one or more emulsifying agents. Various suitable emulsifiers are known in the art and include, for example, fatty acid soaps, preferably calcium soaps, polyamides, sulfonates, triglycerides, and the like. The fatty acid soaps can be formed in situ by the addition of the desired fatty acid and base, preferably lime. The emulsifiers are generally used in amounts of from about 1 to 8 kilograms per cubic meter of drilling fluid.

The drilling fluids also include, as known in the art, one or more additives such as viscosifiers, weighing agents, oil wetting agents and fluid loss preventing agents, to enable the fluids to meet the needs of particular drilling operations. The additives function to keep cutting and debris in suspension, provide the required viscosity, density and additive wetting properties to the fluid, and prevent the loss of liquids from the fluid due to the migration of the liquids into the formations surrounding the well bore.

Clay and polymer viscosifiers such as, for example, bentonite and attapugite (which are sometimes reacted with quaternary ammonium salts), polyacrylates, cellose derivatives, starches, and gums can be used in amounts of from about 0.5 to 5 kilograms per cubic meter of drilling fluid.

The density of the drilling fluid can be increased by using weighing agents such as bartic, galena, iron oxides, siderite and the like, to give densities ranging from about 950 to 2400 kilograms per cubic meter of drilling fluid.

In order to assist in keeping solid additives in suspension in the drilling fluid, oil wetting agents, such as lecithin or organic esters of polyhydric alcohols, can be added in amounts of up to about 4 kilograms per cubic meter of drilling fluid.

Fluid loss agents, such as organophilic humates made by reacting humic acid with amides of polyalkylene polyamines, act to coat the walls of the bore hole and are used in amounts of up to about 7 kilograms per cubic meter of drilling fluid.

An invert drilling fluid was formulated using product formed in Illustrative Example 2 hereinbelow as the base oil, as follows:

200 to 240 grams of the product of Illustrative Example 2

5 to 12 grams of a viscosifier and gelling agent 2 to 10 grams of a basic emulsifier 1 to 3 grams of a surfactant and wetting agent 3 to 9 grams of an emulsifier forming agent 70 to 100 grams of 25% calcium chloride brine solution 100 to 220 grams of a weighing agent The mud was made at a weight of 8 to 14 pounds per gallon and the ingredients listed above were added in the order listed.

Shown in Table 2 are the properties of the product of Illustrative Example 2 hereinbelow and the properties of the above drilling mud containing it. The aging consisted of 16 hours at 122° C. in a hot roll oven. The gel strengths are listed for 10 seconds and 10 minutes, for example, 6/7 for 10 seconds/10 minutes. The mud described above was tested according to the 96 hour $LC_{50}$ mysid shrimp acute toxicity test.

TABLE 2

| Physical Properties of the Product of the Base Oil | |
|---|---:|
| Pour point, ° C. | −28 |
| Viscosity at 4.4° C., cSt | 7.01 |
| Viscosity at 12.8° C., cSt | 5.57 |
| Viscosity at 21.1° C., cSt | 4.52 |
| Viscosity at 40° C., cSt | 3.01 |
| Viscosity at 100° C., cSt | 1.27 |
| Flashpoint, ° C. | 146 |
| Aniline point, ° C. | 81.0 |
| Drilling Mud Properties | |
| Plastic viscosity, cp | 18 |
| Yield point, lbs/100 ft$^2$ | 3 |
| Gel strength, lbs/100 ft$^2$ | 3/4 |
| Electrical stability, volts | 665 |
| After being aged, and hot rolled at 121° C. for 16 hours | |
| Plastic viscosity, cp | 19 |
| Yield point, lbs/100 ft$^2$ | 5 |
| Gel strength, lbs/100 ft$^2$ | 4/5 |
| Electrical stability, volts | 631 |
| Aromatic content, ppm | <1 |
| Mysid Shrimp Toxicity at 96 hours, LC50, ppm | 714,100 |

The present invention will be more clearly understood from the following specific examples. In each of Illustrative Examples 1–23, and Comparative Examples 1–3, the feed was a mixture of approximately 55 weight percent of 1-hexadecene and approximately 45 weight percent of 1-octadecene and approximately I weight percent of n-hexadecane and n-octadecane. The feed contained 63.98 weight percent of vinyl olefins and 28.99 weight percent of vinylidene olefins.

ILLUSTRATIVE EXAMPLES 1–23.

In each of Illustrative Examples 1–23, Engelhard's AL-3996-CR gamma alumina catalyst was loaded into a tubular reactor. In each of Examples 1–8, 450 grams of catalyst was loaded into a 2-inch inside diameter tubular reactor. The catalyst was employed without pretreatment, and the feed was contacted with the catalyst at a weight hourly space velocity of 1.7 kilograms of feed per kilogram of catalyst per hour. In each of Examples 9–23, 10 grams of the catalyst was loaded into a 1-inch inside diameter tubular reactor and was pretreated with a nitrogen purge at 450° C. for 16 hours. The reaction temperatures and gauge pressures, and weight hourly space velocities employed and catalyst turnovers are shown in Table 3. Also shown in Table 3 are the initial and final concentrations of vinyl olefins in the reaction and product mixtures and the pour points of the reaction and product mixtures.

TABLE 3

| Example | Temperature (° C.) | Pressure psig | WHSV (kg/feed/kg catalyst-hr) | Vinyl Olefin (Wt. %) | Catalyst Turnover (kg feed/ kg catalyst) | Cracked Products Produced (Wt. %) | Pour Point (° C.) |
|---|---|---|---|---|---|---|---|
| Feed |  |  |  | 63.2 | 0 | 0 | 1 |
| 1 | 302 | 10 | 1.7 | 2.2 | 10 |  | −29 |
| 2 | 316 | 10 | 1.7 | 2.1 | 12 | .84 | −28 |
| 3 | 322 | 10 | 1.7 | 1.9 | 14 |  | −30 |
| 4 | 333 | 10 | 1.7 | 3.3 | 16 |  | −32 |
| 5 | 343 | 10 | 1.7 | 3.6 | 18 |  | −32 |
| 6 | 282 | 10 | 1.7 | 6.6 | 20 |  | −15 |
| 7 | 287 | 10 | 1.7 | 5.9 | 22 |  | −15 |
| 8 | 304 | 10 | 1.7 | 3.3 | 24 |  | −30 |
| 9 | 280 | 10 | 3 | 1.7 | 24 | .21 | −28 |
| 10 | 310 | 10 | 3 | 1.5 | 64 | .38 | — |
| 11 | 311 | 10 | 1 | 1.2 | 95 |  | −28 |
| 12 | 279 | 10 | 1 | 2.8 | 137 |  | −28 |
| 13 | 280 | 10 | 5 | 8.7 | 184 |  | −28 |
| 14 | 345 | 10 | 3 | 1.4 | 228 | .75 | −28 |
| 15 | 340 | 10 | 1 | 1.3 | 265 |  | −31 |
| 16 | 338 | 10 | 5 | 1.3 | 338 |  | −28 |
| 17 | 311 | 10 | 5 | 2.6 | 372 |  | −28 |
| 18 | 310 | 10 | 3 | 2.3 | 410 | .16 | −28 |
| 19 | 279 | 10 | 1 | 4.5 | 489 |  | −28 |
| 20 | 310 | 40 | 3 | 4.5 | 566 | .11 | −28 |
| 21 | 340 | 40 | 3 | 2.3 | 657 | .36 | −31 |
| 22 | 340 | 40 | 3 | 2.2 | 709 | .37 | −28 |
| 23 | 279 | 40 | 3 | — | 781 | .05 | −28 |

The detailed compositions of the feed employed and product mixtures produced in Examples 2 and 9 are presented in Table 4.

TABLE 4

|  | Feed | Product Mixture of Example 2 | Product Mixture of Example 9 |
|---|---|---|---|
| Concentration, wt. % |  |  |  |
| Vinyl olefins | 64.3 | 2.1 | 1.7 |
| Vinylidene olefins | 27.7 | 2.27 | 1.95 |
| Dimers | 0.07 | <1 | 1.26 |
| Cracked products produced | 0.60 | 0.84 | 0.21 |
| 2-Internal olefins[1] | 4.4 | 12.9 | 17.5 |
| 3-Internal olefins[2] | 1.41 | 22.3 | 20.8 |
| ≧4-Internal olefins[3] | 0.9 | 31.8 | 29.7 |
| 3-Internal olefins plus ≧4-Internal olefins | 2.31 | 54.1 | 50.5 |
| Trisubstituted olefins[4] | 0.29 | 29.41 | 28.43 |
| $CH_3$ groups per olefin | 1.35 | 2.43 | 2.25 |
| $CH_2$ groups per olefin Properties | 13.9 | 12.2 | 13.07 |
| Pour point | 1 | −28 | −28 |

[1]Olefins having the structure of Formula 3
[2]Olefins having the structure of Formula 4
[3]Deep Olefins
[4]Olefins having the structure of Formula 6

COMPARATIVE EXAMPLES

Comparative Example 1

Five grams of Engelhard catalyst X-353, phosphomolybdic acid on titania, 18/40 mesh was loaded into a 1-inch diameter tubular reactor and was purged with nitrogen at 196° C. for 20 hours. Thereafter the catalyst was cooled to room temperature, and the feed was contacted with the catalyst at a weight hourly space velocity of 10 grams of feed per gram of catalyst per hour. Then the temperature of the reactor contents was raised to 125° C. The results are presented in Table 5 and illustrate that this catalyst was essentially completely inactive.

TABLE 5

| Turnover (g/g) | Vinyl, % | Vinylidenes, % | Vinyl Conv, % |
|---|---|---|---|
| 0 (Feed) | 63.98 | 28.99 | — |
| 346 | 63.80 | 22.97 | 0.28 |
| 774 | 63.83 | 26.0 | 0.23 |

Comparative Example 2

Five grams of Engelhard catalyst (0.5% ruthenium on carbon or G-36-1.8/40 mesh) was loaded into a 1-inch diameter tubular reactor and was pretreated with nitrogen at 150° C. for 4 hours. Thereafter the reactor was cooled to room temperature, and the feed was contacted with the catalyst at a weight hourly space velocity of 10 grams of feed per gram of catalyst per hour. Then the temperature of the reactor contents was raised to 125° C. The results are presented in Table 6 and illustrate that this catalyst is also essentially inactive.

TABLE 6

| Turnover (g/g) | Vinyl, % | Vinylidenes, % | Vinyl Conv, % |
|---|---|---|---|
| 0 (Feed) | 63.98 | 28.99 | — |
| 225 | 63.05 | 28.64 | 1.45 |
| 631 | 63.36 | 28.62 | 0.97 |

Comparative Example 3

Five grams of gamma-alumina catalyst (Engelhard Al-3996-CR) was loaded into a 1-inch diameter tubular reactor and was pretreated with nitrogen at 150° C. for 18 hours. The catalyst was then cooled to room temperature and the feed was contacted with the catalyst at a space velocity of 10 grams of feed per gram of catalyst per hour. The reactor temperature was raised to 125° C. Subsequently, in order to increase the catalyst activity, the temperature was raised to 180° C. and the weight hourly space velocity was reduced to about 5. The results are presented in Table 7 and illustrate that this catalyst is also substantially inactive.

TABLE 7

| Turnover (g/g) | Vinyl, % | Vinylidenes, % | Vinyl Conv, % |
|---|---|---|---|
| 0 (Feed) | 63.98 | 28.99 | — |
| 183 (10 WHSV, 125° C.) | 61.8 | 27.71 | 3.41 |
| 287 (10 WHSV, 125° C.) | 63.73 | 28.61 | 0.39 |
| 398 (4.9 WHSV, 180° C.) | 63.65 | 28.28 | 0.52 |
| 622 (5.0 WHSV, 180° C.) | 63.83 | 28.43 | 0.23 |

From the above description, it is apparent that, while only certain embodiments are described, it is to be understood that these are for illustrative purposes only. Many alternatives, modifications and variations will be apparent to those skilled in the art, and these are considered equivalents and are within the spirit and scope of the present invention.

That which is claimed is:

1. A method for isomerizing an alpha olefins mixture comprising vinyl and vinylidene olefins containing from 10 to 35 carbon atoms, comprising: contacting the alpha olefin mixture in the gas or liquid phase with a bed of porous solid acid catalyst particles comprising gamma alumina having a specific surface area of at least 100 square meters per gram, a pore volume of at least 0.4 cubic centimeter per gram, an average pore diameter of at least 30 Angstroms, a sodium content of less than 0.01 weight percent and an ammonia chemisorption of at least 0.1 millimole per gram, at a reaction temperature in the range of from about 200° C. to about 400° C., a reaction pressure in the range of from about 15 to about 500 pounds per square inch absolute and a weight hourly space velocity of from about 0.5 to about 20 kilograms of olefin mixture per kilogram of catalyst particles per hour, wherein the reaction temperature, pressure and weight hourly space velocity are selected so as to form a product mixture comprising at least 70 weight percent of di- and tri-substituted internal olefins, of which product mixture at least 20 weight percent are tri-substituted internal olefins, at least 20 weight percent of which product mixture are di-substituted internal olefins having a double bond at the fourth or higher numbered carbon atom position, less than 50 weight percent of which are di-substituted internal olefins having a double bond at the second or third numbered carbon atom position, and which has a kinematic viscosity less than 4 cSt measured at 40° and a pour point below −25° C., less than 40 weight percent of the internal olefins produced are di-substituted internal olefins having a double bond at the second or third numbered carbon atom position, and wherein at least forty-five percent of the internal olefins produced are the sum of the internal olefins having a double bond at the third numbered carbon atom position plus the internal olefins having a double bond at the fourth or higher numbered carbon atom position.

2. The method of claim 1 wherein the alpha olefin mixture consists essentially of olefins containing from 16 to 18 carbon atoms.

3. The method of claim 1 wherein the product mixture comprises at least 80 weight percent of di- or tri-substituted internal olefins.

4. The method of claim 1 wherein at least 25 weight percent of the internal olefins produced are di-substituted internal olefins having a double bond at the fourth or higher numbered carbon atom position.

5. The method of claim 1 wherein the product mixture comprises at least 25 weight percent of tri-substituted internal olefins.

6. The process of claim 1 wherein the product mixture has a pour point lower than about −30° C.

7. The process of claim 1 wherein the product mixture has a kinematic viscosity less than about 3.5 centistokes6 measured at 40° C. temperature.

8. The process of claim 1 wherein the solid catalyst particles have pores that have an average pore diameter of at least 40 Angstroms.

9. The process of claim 1 wherein the solid catalyst particles comprise at least 99.5 weight percent of gamma alumina.

10. The process of claim 9 wherein the solid catalyst particles comprise at least 99.0 weight percent of gamma alumina.

11. The process of claim 1 wherein the reaction temperature is in the range of from about 250° C. to about 350° C.

12. The process of claim 1 wherein the weight hourly space velocity is in the range of from about 1 to about 15 pounds of the olefin mixture per pound of catalyst particles per hour.

* * * * *

UNITED STATES PATENT AND TRADEMARK OFFICE
CERTIFICATE OF CORRECTION

PATENT NO. : 6,407,302 B1  Page 1 of 1
DATED : June 18, 2002
INVENTOR(S) : Fred Chun-Chien Twu and William L. Cox It is certified that error appears in the above-identified patent and that said Letters Patent is hereby corrected as shown below:

Column 2,
Line 20, "desirable features of comprisi di-" should read -- desirable features of comprising both di- --

Column 4,
Line 18, "to about 50, hounds" should read -- to about 50, pounds --

Column 5,
Line 4, "internal olefins: of Formula 6." should read -- internal olefins of Formula 6. --

Column 6,
Line 64, "approximately I weight percent" should read -- approximately 1 weight percent --

Column 8,
Line 67, "carbon or G-36, 1.8/40 mesh)" should read -- carbon or G-36, 18/40 mesh) --

Column 9,
Line 21, "A1-3996-CR) was loaded" should read -- AI-3996-CR) was loaded --

Column 10,
Line 43, "less than about 3.5 centistokes6" should read -- less than about 3.5 centistokes --

Signed and Sealed this

Fifteenth Day of October, 2002

*Attest:*

*Attesting Officer*

JAMES E. ROGAN
*Director of the United States Patent and Trademark Office*